US009014340B2

(12) United States Patent
Kurochi

(10) Patent No.: US 9,014,340 B2
(45) Date of Patent: Apr. 21, 2015

(54) RADIATION TOMOGRAPHY SYSTEM, RADIATION DETECTING DEVICE, AND SPATIAL RESOLUTION CHANGING METHOD FOR RADIATION TOMOGRAPHY

(71) Applicant: GE Medical Systems Global Technology Company, LLC, Waukesha, WI (US)

(72) Inventor: Haruo Kurochi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 267 days.

(21) Appl. No.: 13/722,242

(22) Filed: Dec. 20, 2012

(65) Prior Publication Data

US 2013/0163715 A1 Jun. 27, 2013
US 2014/0016738 A9 Jan. 16, 2014

(30) Foreign Application Priority Data

Dec. 21, 2011 (JP) .................................. 2011-279323

(51) Int. Cl.
*G21K 1/02* (2006.01)
*A61B 6/03* (2006.01)
*A61B 6/00* (2006.01)
*A61B 6/06* (2006.01)

(52) U.S. Cl.
CPC ... *G21K 1/02* (2013.01); *A61B 6/00* (2013.01); *A61B 6/035* (2013.01); *A61B 6/06* (2013.01)

(58) Field of Classification Search
CPC ....... A61B 6/4266; A61B 6/4291; G21K 1/02
USPC .............. 378/4, 19, 147, 149, 154; 250/363.1
See application file for complete search history.

(56) References Cited

U.S. PATENT DOCUMENTS

| 7,612,343 | B2 | 11/2009 | Vickers |
| 7,844,032 | B2 | 11/2010 | Vermilyea et al. |
| 7,916,839 | B2 * | 3/2011 | Halazonetis et al. ......... 378/147 |
| 8,126,119 | B2 * | 2/2012 | Kurochi ....................... 378/147 |
| 8,139,717 | B2 | 3/2012 | Harding et al. |
| 2009/0225955 | A1 | 9/2009 | Igarashi et al. |

(Continued)

FOREIGN PATENT DOCUMENTS

| JP | 60122874 | 8/1985 |
| JP | 2005526967 | 9/2005 |

(Continued)

*Primary Examiner* — Nikita Wells
(74) *Attorney, Agent, or Firm* — Armstrong Teasdale LLP

(57) ABSTRACT

A radiation tomography system is provided. The radiation tomography system includes a radiation source configured to rotate around a subject and apply radiation to the subject, a plurality of radiation detecting elements disposed opposite the radiation source, a plurality of collimator plates partitioning the radiation detecting elements in a channel direction, the collimator plates erected such that plate surfaces of each of the plurality of collimator plates extend along a direction of radiation from the radiation source, and an aperture-width changing unit configured to change a width of each aperture formed by the plurality of collimator plates by moving a plurality of radiation absorbing members along respective end sides of the collimator plates close to the radiation source, the plurality of radiation absorbing members moveable between a first position at which the end sides are covered and a second position at which the end sides are exposed.

20 Claims, 5 Drawing Sheets

(56) References Cited

U.S. PATENT DOCUMENTS

2011/0096895 A1    4/2011  Kurochi
2012/0219107 A1*   8/2012  Kurochi et al. ................. 378/19
2013/0223588 A1*   8/2013  Kurochi et al. ................. 378/19

FOREIGN PATENT DOCUMENTS

JP    2009285050    12/2009
WO    2010077626    7/2010

* cited by examiner

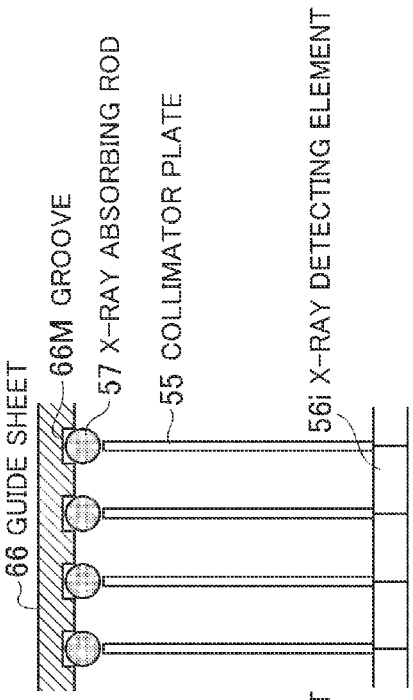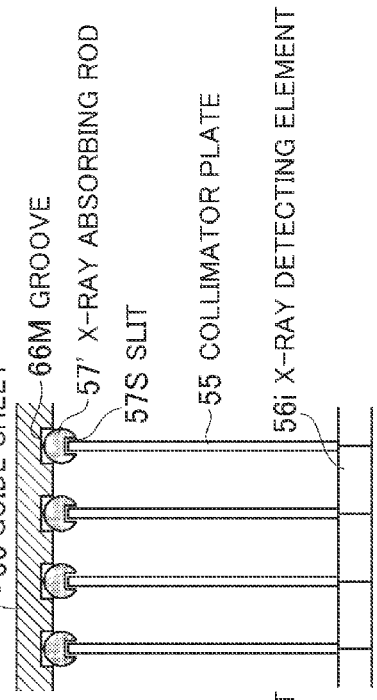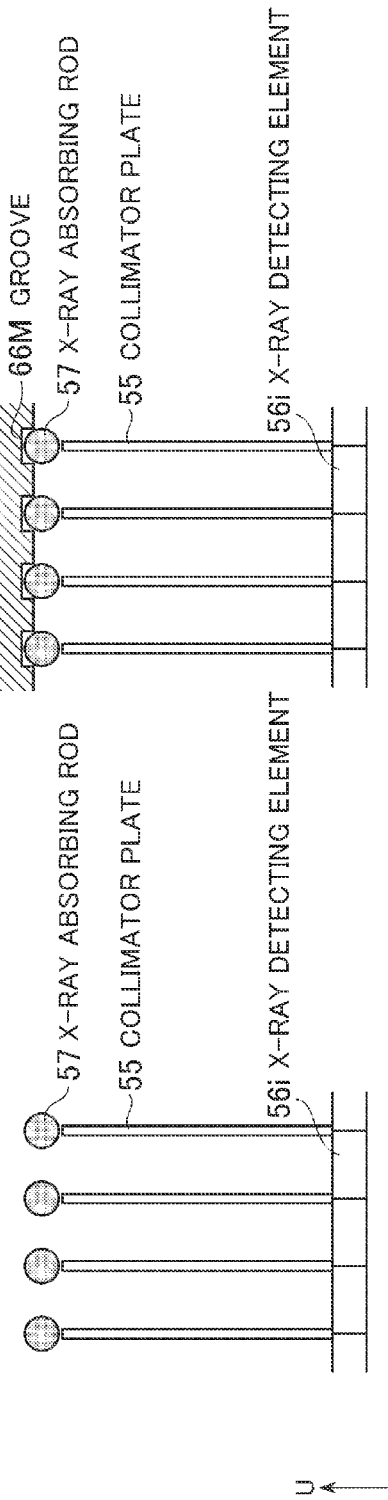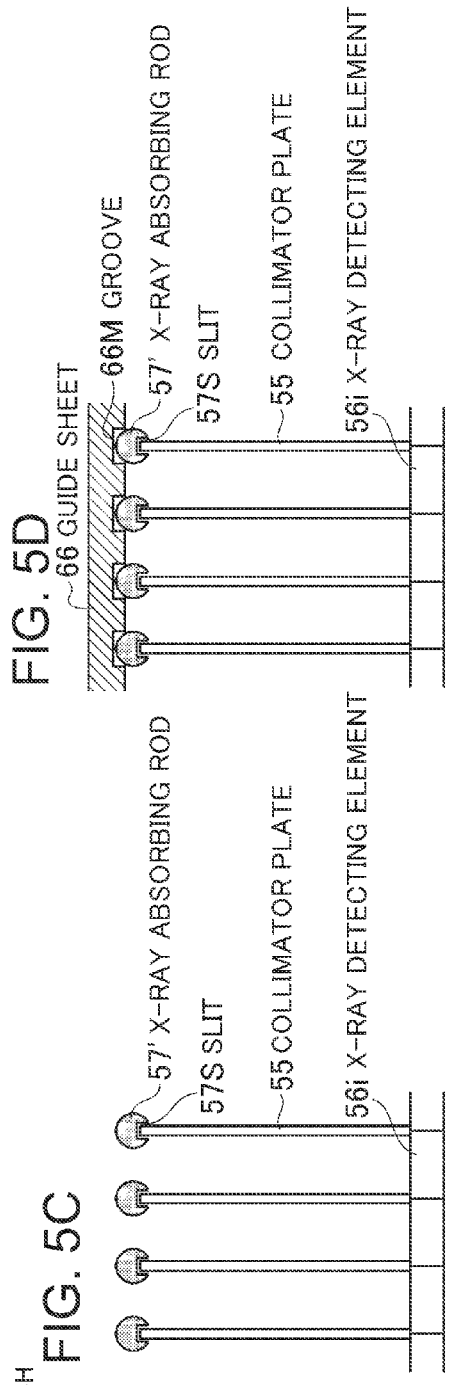

US 9,014,340 B2

RADIATION TOMOGRAPHY SYSTEM, RADIATION DETECTING DEVICE, AND SPATIAL RESOLUTION CHANGING METHOD FOR RADIATION TOMOGRAPHY

CROSS REFERENCE TO RELATED APPLICATIONS

This application claims the benefit of Japanese Patent Application No. 2011-279323 filed Dec. 21, 2011, which is hereby incorporated by reference in its entirety.

BACKGROUND OF THE INVENTION

The present invention relates to a technology which improves a spatial resolution in radiation tomography.

It is known that it is possible to improve a spatial resolution in radiation tomography by partially covering an aperture portion formed by collimators provided in a radiation detector with a shield etc. to narrow the aperture. Specifically, in order to achieve it, there is proposed a method to so dispose a "diaphragm" on a surface of the radiation detector as to cover edge portions of detecting elements (see Japanese Patent Application Laid-Open No. 2005-526967, Abstract). This "diaphragm" is constituted by combining strip-like pieces extending in a spreading direction of radiation emitted from a radiation source and in a rotary axis direction (z direction) of the radiation source.

If detection surfaces of detecting elements which constitute a radiation detector are covered partially, a spatial resolution will improve, but the use efficiency of radiation falls that much. Therefore, in radiation tomography, it is not desirable in terms of exposure to radiation to maintain a high spatial resolution using this technique. Therefore, in reality, the spatial resolution may be improved by this method only when a higher spatial resolution is necessary even if it sacrifices radiation use efficiency and, in other cases, radiographs may be taken in a normal state. That is, a method of attaching and detaching a "diaphragm" as required is conceivable.

However, in order to attach and detach the "diaphragm" constituted by combining the above strip-like pieces, it requires a large-scale and complicated attach/detach mechanism, being disadvantageous in terms of cost and space. Further, it is not easy to perform precise alignment. Therefore, the method of attaching and detaching the "diaphragm" is not suitable for changing the spatial resolution in radiation tomography.

Under these circumstances, there is called for a technology which makes it possible to switch a spatial resolution in radiation tomography with a simple structure.

BRIEF DESCRIPTION OF THE INVENTION

In a first aspect, a radiation tomography system is provided. The radiation tomography system includes a radiation source rotating around a subject to be imaged and applying radiation to the subject to be imaged, a plurality of radiation detecting elements so disposed as to be opposed to the radiation source, a plurality of collimator plates partitioning the plurality of radiation detecting elements in a channel direction of the radiation detecting elements, the plurality of collimator plates being erected such that respective plate surfaces are disposed along a direction of radiation from the radiation source, and an aperture-width changing unit which changes a width of each aperture formed by the plurality of collimator plates by moving a plurality of radiation absorbing members extending in an end side direction of respective end portions, being close to the radiation source, of the plurality of collimator plates to a first position at which the end portions are covered and to a second position at which the end portions are exposed along end sides of the end portions.

In a second aspect, a radiation tomography system of the first aspect is provided, wherein, when the plurality of radiation absorbing members are moved to the first position to be disposed, the aperture-width changing unit has a plurality of receiving parts for receiving respective tip portions of the plurality of radiation absorbing members.

In a third aspect, a radiation tomography system of the first or second aspect is provided, wherein the aperture-width changing unit has a radiation transmittable member which guides the plurality of radiation absorbing members in the end side direction of the end portions.

In a fourth aspect, a radiation tomography system of the third aspect is provided, wherein the radiation transmittable member contains carbon fibers.

In a fifth aspect, a radiation tomography system of any of the first to fourth aspects is provided, wherein each of the plurality of radiation absorbing members has a groove into which the end portion, being close to the radiation source, of the collimator plate is fitted; and wherein the aperture-width changing unit moves the plurality of radiation absorbing members with the end portions being fitted in the grooves.

In a sixth aspect, a radiation tomography system of any of the first to fifth aspects is provided, wherein the plurality of radiation absorbing members contain lead, molybdenum, tungsten, or an alloy of molybdenum or tungsten.

In a seventh aspect, a radiation tomography system of any of the first to sixth aspects is provided, wherein the plurality of radiation absorbing members are formed such that an axis cross-section thereof is substantially circular or rectangular.

In an eighth aspect, a radiation detecting device is provided. The radiation detection devices includes a plurality of radiation detecting elements so provided as to be opposed to a radiation source applying radiation to a subject to be imaged, a plurality of collimator plates partitioning the plurality of radiation detecting elements in a channel direction of the radiation detecting elements, the plurality of collimator plates being erected such that respective plate surfaces are disposed along a direction of radiation from the radiation source, and an aperture-width changing unit which changes a width of each aperture formed by the plurality of collimator plates by moving a plurality of radiation absorbing members extending in an end side direction of respective end portions, being closer to the radiation source, of the plurality of collimator plates to a first position at which the end portions are covered and to a second position at which the end portions are exposed along the end sides of the end portions.

In a ninth aspect, a radiation detecting device of the eighth aspect is provided, wherein, when the plurality of radiation absorbing members are moved to the first position to be disposed, the aperture-width changing unit has a plurality of tip portion receiving parts for receiving respective tip portions of the plurality of radiation absorbing members.

In a tenth aspect, a radiation detecting device of the eighth or ninth aspect is provided, wherein the aperture-width changing unit has a radiation transmittable member which guides the plurality of radiation absorbing members in the end side direction of the end portions.

In an eleventh aspect, a radiation detecting device of the tenth aspect is provided, wherein the radiation transmittable member contains carbon fibers.

In a twelfth aspect, a radiation detecting device of any of the eighth to eleventh aspects is provided, wherein each of the plurality of radiation absorbing members has a groove into which the end portion, being closer to the radiation source, of the collimator plate fits, and wherein the aperture-width changing unit moves the plurality of radiation absorbing members with the end portions being fitted in the grooves, respectively.

In a thirteenth aspect, a radiation detecting device of any of the eighth to twelfth aspects is provided, wherein the plurality of radiation absorbing members contain lead, molybdenum, tungsten, or an alloy of molybdenum or tungsten.

In a fourteenth aspect, a radiation detecting device of any of the eighth to thirteenth aspects is provided, wherein the plurality of radiation absorbing members are formed such that each of the axis cross-sections thereof is substantially circular or rectangular.

In a fifteenth aspect, a method of switching a spatial resolution in radiation tomography with use of a radiation detecting device is provided. The radiation detection device includes a plurality of radiation detecting elements so disposed as to be opposed to a radiation source applying radiation to a subject to be imaged, and a plurality of collimator plates partitioning the plurality of radiation detecting elements in a channel direction of the radiation detecting elements, the plurality of collimator plates being erected such that respective plate surfaces are disposed along a direction of radiation from the radiation source, wherein a width of each aperture formed by the plurality of collimator plates is changed by moving a plurality of radiation absorbing members extending in an end side direction of respective end portions, being close to the radiation source, of the plurality of collimator plates to a first position at which the end portions are covered and to a second position at which the end portions are exposed along the end sides of the end portions.

According to the above aspects, the width of each aperture formed by the plurality of collimator plates is changed by moving the plurality of radiation absorbing members extending in the end side direction of the respective end portions, being close to the radiation source, of the plurality of collimator plates to the first position at which the end portions are covered and to the second position at which the end portions are exposed along the end sides of the end portions. Therefore, simply by linearly moving the radiation absorbing members for a short distance, the width of the aperture for the radiation beam entering the radiation detecting element can be changed, and the spatial resolution in the radiation tomography can be changed with a simple structure.

BRIEF DESCRIPTION OF THE DRAWINGS

FIGS. 5A-5D show variations of a mechanism related to movement of the X-ray absorbing rod.

DETAILED DESCRIPTION OF THE INVENTION

Here, exemplary embodiments will be described, although the disclosure is not limited to those embodiments specifically described herein.

Figure 1:
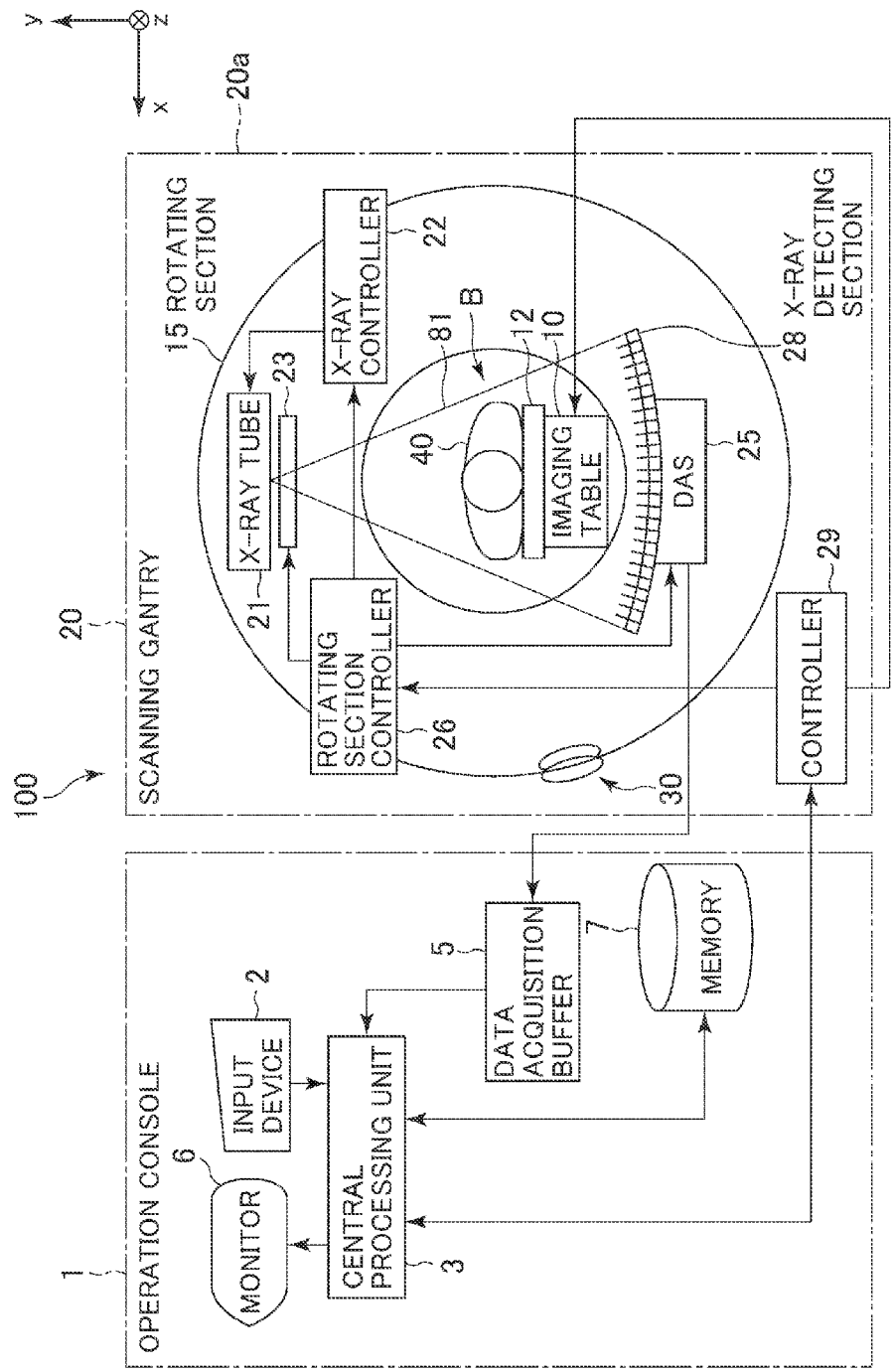
FIG. 1 is a schematic view showing a construction of an X-ray CT apparatus according to an exemplary embodiment.

FIG. 1 schematically shows a construction of an X-ray CT apparatus according to an exemplary embodiment.

The X-ray CT apparatus 100 includes an operation console 1, an imaging table 10, and a scanning gantry 20.

The operation console 1 includes an input device 2 which receives data inputted from an operator, a central processing unit 3 which controls each section for imaging a subject and performs data processing for generating an image, a data acquisition buffer 5 which collects data acquired by the scanning gantry 20, a monitor 6 which displays the image, and memory 7 in which programs and data, etc. are stored.

The imaging table 10 has a cradle 12 which conveys a subject 40 mounted thereon to an opening B of the scanning gantry 20. The cradle 12 is moved up and down and, also, moved horizontally in a linear manner by motors built in the imaging table 10. In this regard, it is assumed that a body axis direction of the subject 40, namely, a horizontally moving direction of the cradle 12 is "z" direction, a vertical direction is "y" direction, and a direction perpendicular to the z direction and the y direction, being a horizontal direction, is "x" direction.

The scanning gantry 20 has a rotating section 15, and a body portion 20a which rotatably supports the rotating section 15. Mounted on the rotating section 15 are an X-ray tube 21, an X-ray controller 22 which controls the X-ray tube 21, an aperture 23 through which X-ray 81 generated in the X-ray tube 21 is formed into a fan beam or a cone beam, an X-ray detecting section 28 which detects the X-ray 81 having passed through the subject 40, a DAS (also called a "Data Acquisition System") 25 which converts the output from the X-ray detecting section 28 into X-ray projection data and acquires them, and a rotating section controller 26 for controlling the X-ray controller 22, the aperture 23, and the DAS 25. The body portion 20a has a controller 29 which sends and receives control signals etc. to and from the operation console 1 and the imaging table 10. The rotating section 15 and the body portion 20a are electrically connected through a slip ring 30.

The X-ray tube 21 and the X-ray detecting section 28 are disposed sandwiching an imaging space in which the subject 40 is placed, namely, a hollow portion B of the scanning gantry 20, and are opposed to each other. When the rotating section 15 rotates, the X-ray tube 21 and the X-ray detecting section 28 rotate, while maintaining their positional relationship, around the subject 40. The X-ray 81 from the X-ray tube 21 being formed into the fan beam in the shape of a fan or the cone beam by the aperture 23 passes through the subject 40 and is applied to a detection plane of the X-ray detecting section 28. A direction of the X-ray 81 being the fan beam or the cone beam spreading in an xy plane is called a "channel direction (CH direction)."

Figure 2:
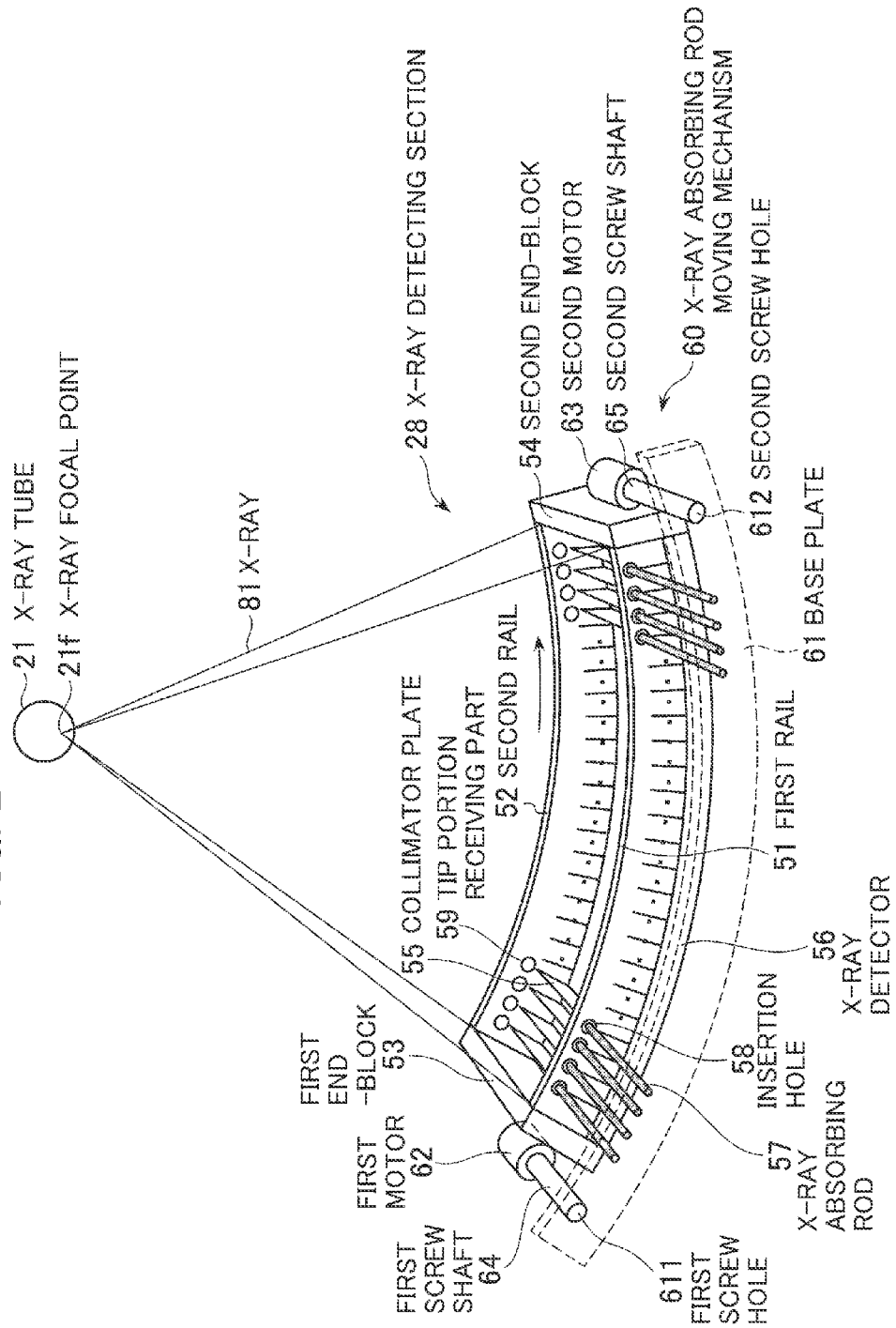
FIG. 2 is a perspective view of an X-ray detecting section.
Figure 3:
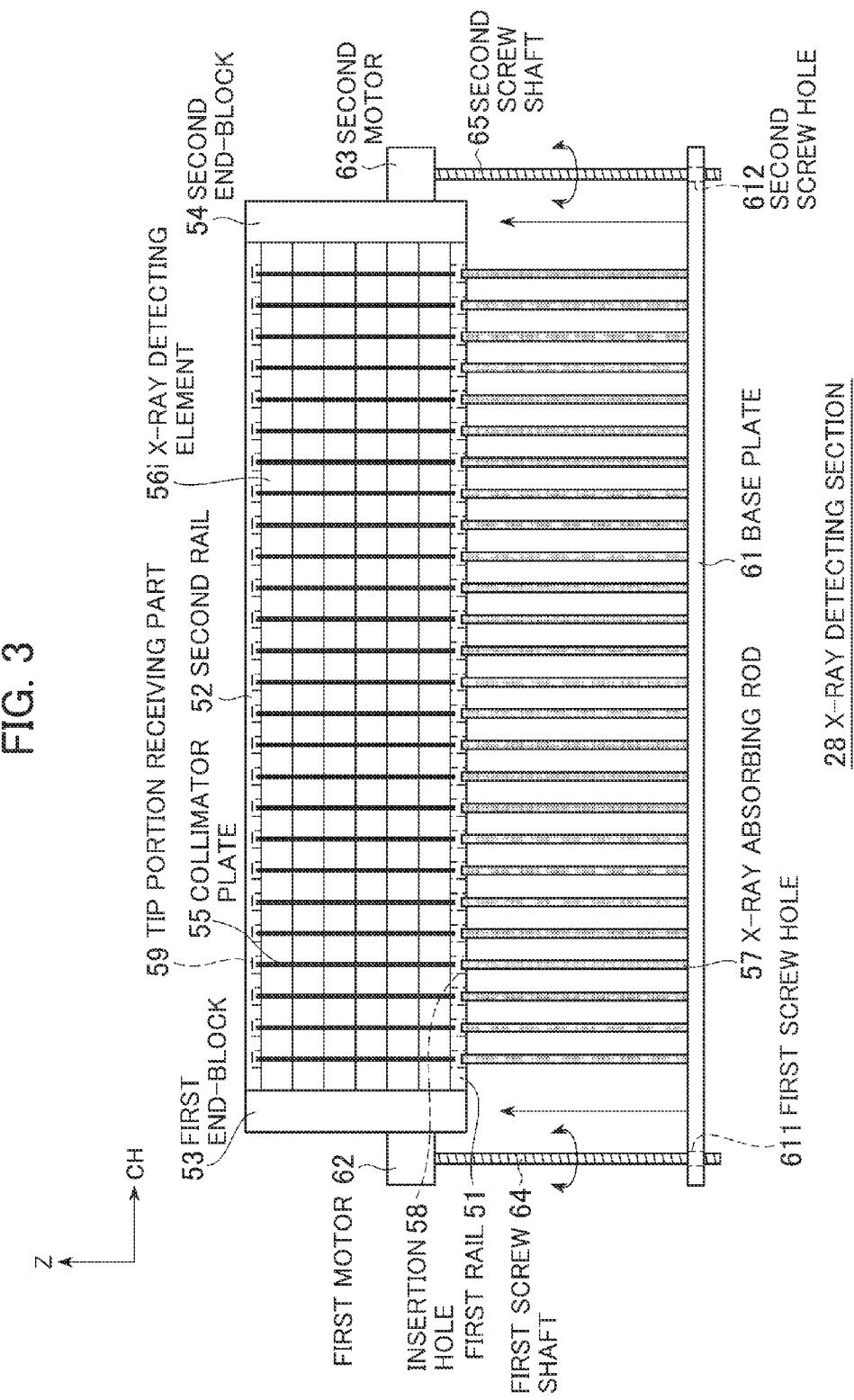
FIG. 3 shows the X-ray detecting section when an X-ray absorbing rod is removed from an upper side of a collimator plate.

FIGS. 2 and 3 show examples of a construction of the X-ray detecting section 28. FIG. 2 is a perspective view of the X-ray detecting section 28, and FIG. 3 shows a view of the X-ray detecting section 28 as seen from the location of the X-ray tube 21.

The X-ray detecting section 28 includes a frame 50, a plurality of collimator plates 55, an X-ray detector 56, a plurality of X-ray absorbing rods 57, and an X-ray absorbing rod moving mechanism 60. Here the plurality of X-ray absorbing rods 57 and the X-ray absorbing rod moving mechanism 60 are an example of the aperture-width changing unit.

The frame 50 includes first and second rails 51 and 52, and first and second end-blocks 53 and 54. Each of the first and second rails 51 and 52 is in the strip-like shape, extending in the channel direction in a curved manner. They are so disposed as to be parallel to each other in the z direction at predetermined intervals. The first and second end-blocks 53 and 54 are so provided as to connect the first and second rails 51 and 52 at both ends thereof in the channel direction.

The X-ray detector 56 is disposed on the X-ray output side of the frame 50. The X-ray detector 56 comprises a plurality of X-ray detecting elements 56$i$ provided in a matrix-like arrangement in the channel direction and the z direction. About 1000×32 pieces of X-ray detecting elements 56$i$, for example, are arranged in the channel direction and the z direction.

The plurality of collimator plates 55 are supported and extend between the first rail 51 and the second rail 52 and are so provided as to partition the X-ray detecting elements 56$i$ in the channel direction. Moreover, the plurality of collimator plates 55 are erected such that respective plate surfaces are disposed along a direction of radiation from an X-ray focal point of the X-ray tube 21. Dimensions of the collimator plate 55 include, for example, a width of 30 to 40 millimeters (mm) in the z direction, a width of 25 mm in a height direction, and a plate thickness of 0.2 mm. Moreover, a pitch of the X-ray detecting elements 56$i$ in the channel direction, namely, a pitch of the collimator plates 55 in the channel direction is, for example, 0.8 mm.

In FIGS. 2 and 3, for the sake of illustration, smaller number of X-ray detecting elements 56$i$ and the collimator plates 55 are shown.

Each of the collimator plates 55 is provided with one X-ray absorbing rod 57. The X-ray absorbing rod 57 has a substantially circular axis cross-section, and is in the substantial cylindrical shape. The longitudinal size of the X-ray absorbing rod 57 is, for example, a little greater than the width of the collimator plate 55 in the z direction, and the X-ray absorbing rod 57 has a diameter of 0.5 mm. The X-ray absorbing rod 57 contains, for example, lead, tungsten, molybdenum, or an alloy of tungsten or molybdenum etc.

The X-ray absorbing rod 57 may have a rectangular axis cross-section or the like other than circular ones, which enables easy processing and reduction in manufacturing cost. The X-ray absorbing rods 57 may be provided to some of all the collimator plates 55 which are closer to the center in the channel direction. A region whose spatial resolution is to be improved is located in the central part of the imaging field of view in many cases. Therefore, the above method does not practically cause a problem, lowering the manufacturing cost.

In the first rail 51, at a position on an upper side of an upper end portion closer to the X-ray tube 21 of the collimator plate 55 supported by the first rail 51, an insertion hole 58 into which the X-ray absorbing rod 57 is inserted is formed for each collimator plate 55.

The X-ray absorbing rod moving mechanism 60 inserts the plurality of X-ray absorbing rods 57 into the insertion holes 58, respectively, from the outside of the frame 50, and moves the plurality of X-ray absorbing rods 57 along end sides of the upper end portions, being close to the corresponding X-ray tube 21, of the collimator plates 55. Accordingly, the X-ray absorbing rod moving mechanism 60 can move the plurality of X-ray absorbing rods 57 to a first position at which the respective upper end portions, being close to the X-ray tube 21, of the collimator plates 55 are covered and to a second position at which the upper end portions are exposed. As a result, the width of each aperture formed by the plurality of collimator plates 55 can be changed.

According to the exemplary embodiment, the X-ray absorbing rod moving mechanism 60 includes a base plate 61, first and second motors 62 and 63, first and second screw shafts 64 and 65, and a plurality of tip portion receiving parts 59 provided in a side surface inside the second rail 52.

One end portion of each X-ray absorbing rod 57 is fixed to the base plate 61. Moreover, in both the ends of the base plate 61 in the channel direction, first and second screw holes 611 and 612 are formed. The first motor 62 is provided in the first end-block 53. The first screw shaft 64 whose axial direction corresponds to the z direction is connected to a motor shaft of the first motor 62 directly or through a gear. The first screw shaft 64 is fitted into the first screw hole 611 in the base plate 61. Similarly, the second motor 63 is provided in the second end-block 54. The second screw shaft 65 whose axial direction corresponds to the z direction is connected to a motor shaft of the second motor 63 directly or through a gear. The second screw shaft 65 is inserted into the second screw hole 612 of the base plate 61. Accordingly, when the first and second motors 62 and 63 are driven, the first and second screw shafts 64 and 65 are rotated and the base plate 61 is moved in the z direction. The direction in which the base plate 61 is moved is controlled by switching the direction in which the first and second motors 62 and 63 are driven to rotate.

In addition, a rack-and-pinion, an air cylinder, etc. may be used for the X-ray absorbing rod moving mechanism 60.

On a side surface inside the second rail 52, at a position on an upper side of the upper end portion closer to the X-ray tube 21 of the collimator plate 55 supported by the second rail 52, a tip portion receiving part 59 for receiving the tip portion of the X-ray absorbing rod 57 is formed for each collimator plate 55. The tip portion receiving part 59 is, for example, a recess. It is formed such that an opening portion is larger than a bottom portion, and it aligns the X-ray absorbing rod 57 by guiding it to a predetermined position. Also, the tip portion receiving part 59 is not an indispensable component.

The movement of the X-ray absorbing rod 57 by the X-ray absorbing rod moving mechanism 60 is controlled by the central processing unit 30.

In a scanning plan, when an operator selects a normal resolution mode, the central processing unit 30 controls the X-ray absorbing rod moving mechanism 60 and, as shown in FIG. 3, moves each X-ray absorbing rod 57 to the second position at which the upper end portion of each collimator plate 55 is exposed.

Figure 4:
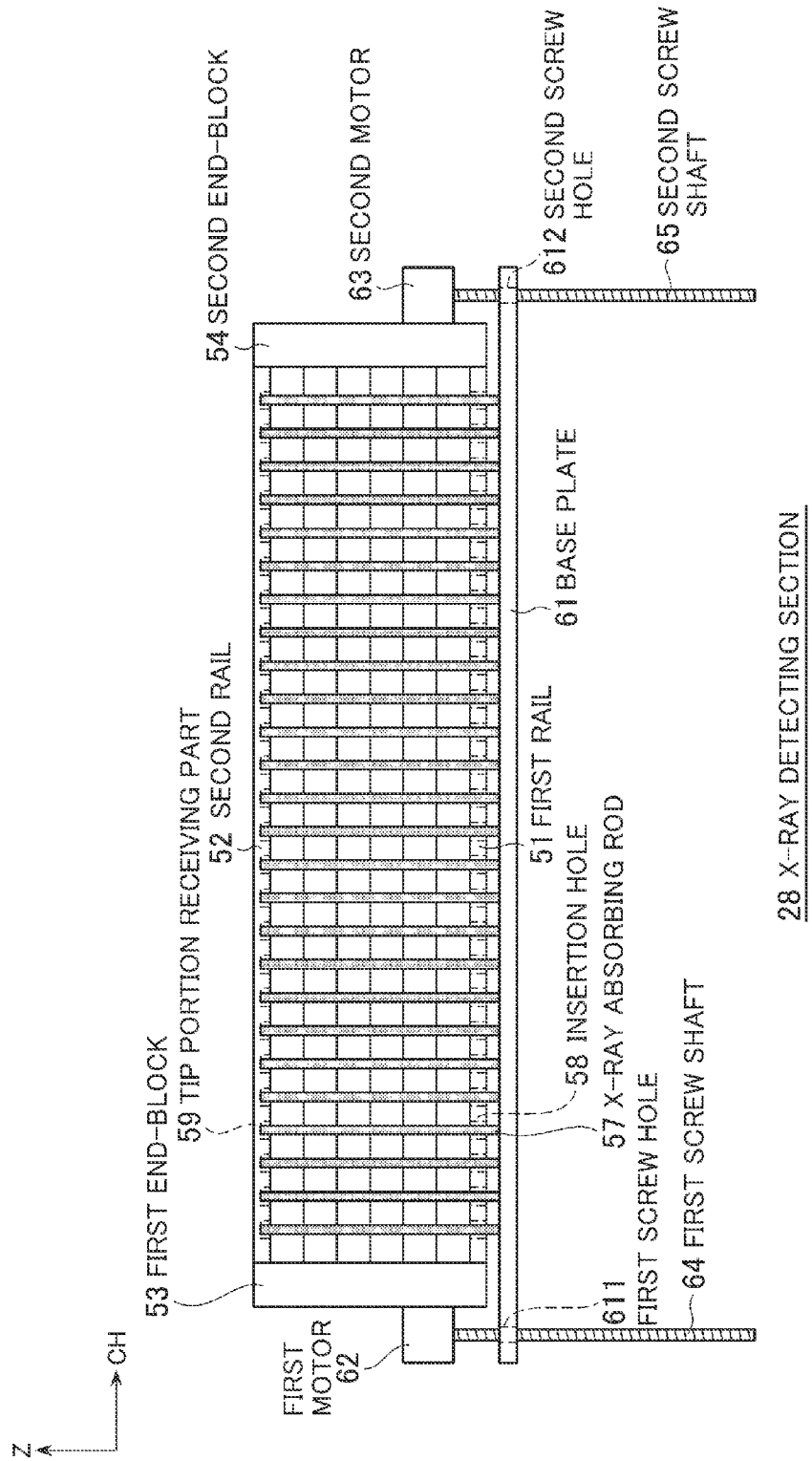
FIG. 4 shows the X-ray detecting section when the X-ray absorbing rod is inserted in the upper side of the collimator plate.

On the other hand, if the operator selects a high resolution mode in the scanning plan, the central processing unit 30 controls the X-ray absorbing rod moving mechanism 60 and, as shown in FIG. 4, moves each X-ray absorbing rod 57 to the first position at which the upper end portion of each collimator plate 55 is covered. In this regard, in order to cover reduction in X-ray utilization factor, an image reconstruction method (for example, "ASiR" in the X-ray CT apparatus made by GE Healthcare) to which a iterative reconstruction method is applied may be used as an image reconstruction method. Accordingly, it becomes possible to suppress an image noise and to perform photographing with a high spatial resolution without increasing the amount of X-ray radiation to be emitted.

FIGS. 5A-5D show variations of the mechanism related to movement of the X-ray absorbing rod. Also, in FIGS. 5A-5D, a horizontal direction is referred to as a "channel direction (CH)" and a vertical direction is referred to as a "direction (U)" toward the X-ray focal point 21$f$.

FIG. 5A shows an example in which the cylindrical X-ray absorbing rod 57 is put in and taken out in the z direction on the upper side of the upper end portion of the collimator plate 55.

FIG. 5B shows an example where there is provided a guide sheet 66 in which grooves 66M for partially receiving surfaces of the cylindrical X-ray absorbing rods 57 are formed along the end side direction of the upper end portions of the collimator plates 55. The guide sheet 66 is fixed to the frame 50. By the guide sheet 66, the X-ray absorbing rod 57 is guided in the z direction without deviating from the right course. The guide sheet 66 comprises an X-ray transmittable member and is, for example, a resin or the like containing light and strong carbon fibers. In addition, a cross-section of the groove 66M may be in the shape of "U", "V", and "arc" or the like.

FIG. 5C shows an example where an X-ray absorbing rod 57' in which a slit 57S for the upper end portion of the collimator plate 55 to be fitted in is formed is put into and taken out of the cylindrical X-ray absorbing rod 57, with the upper end portion of the collimator plate 55 being fitted in the slit 57S, in the z direction. Because of the slit 57S, the X-ray absorbing rod 57' is guided in the z direction without deviating from the right course.

FIG. 5D shows an example of combining the examples shown in FIGS. 5B and 5C. The deviation of the X-ray absorbing rod 57' is suppressed more reliably so as to guide the X-ray absorbing rod 57' in the z direction.

According to the embodiments described above, the plurality of X-ray absorbing rods 57 for covering the upper end portions, being close to the X-ray tube 21, of the plurality of collimator plates 55 are moved to the first position at which the upper end portions are covered and to the second position at which the upper end portions are exposed along the end sides of the upper end portions. In this way, the width of the aperture for the X-ray entering the X-ray detecting element 56i can be changed simply by linearly moving the X-ray absorbing rod 57 for a short distance. Thus, it becomes possible to switch the spatial resolution in the X-ray tomography with a simple structure. As a result, it becomes possible to incorporate a spatial resolution switching function into the X-ray CT apparatus at a low cost in a space saving manner.

An X-ray CT apparatus has been used in the embodiment described above. However, the methods and systems described herein are applicable also to a PET-CT system and a SPECT-CT system in which an X-ray CT apparatus and a PET system or a SPECT system are combined.

What is claimed is:

1. A radiation tomography system, comprising:
a radiation source configured to rotate around a subject to be imaged and apply radiation to the subject;
a plurality of radiation detecting elements disposed opposite the radiation source;
a plurality of collimator plates partitioning the plurality of radiation detecting elements in a channel direction of the radiation detecting elements, the plurality of collimator plates erected such that plate surfaces of each of the plurality of collimator plates extend along a direction of radiation from the radiation source; and
an aperture-width changing unit configured to change a width of each aperture formed by the plurality of collimator plates by moving a plurality of radiation absorbing members along respective end sides of the collimator plates close to the radiation source, the plurality of radiation absorbing members moveable between a first position at which the end sides are covered and a second position at which the end sides are exposed.

2. A radiation tomography system according to claim 1, where the aperture-width changing unit has a plurality of receiving parts configured to receive respective tip portions of the plurality of radiation absorbing members when the plurality of radiation absorbing members are moved to the first position.

3. A radiation tomography system according to claim 1, wherein the aperture-width changing unit includes a radiation transmittable member configured to guide the plurality of radiation absorbing members along the respective end sides.

4. A radiation tomography system according to claim 2, wherein the aperture-width changing unit includes a radiation transmittable member configured to guide the plurality of radiation absorbing members along the respective end sides.

5. A radiation tomography system according to claim 3, wherein the radiation transmittable member contains carbon fibers.

6. A radiation tomography system according to claim 4, wherein the radiation transmittable member contains carbon fibers.

7. A radiation tomography system according to claim 1, wherein each of the plurality of radiation absorbing members includes a groove into which the end side of the respective collimator plate fits wherein the aperture-width changing unit is configured to move the plurality of radiation absorbing members with the end sides fitted in the grooves.

8. A radiation tomography system according to claim 1, wherein the plurality of radiation absorbing members contain lead, molybdenum, tungsten, or an alloy of molybdenum or tungsten.

9. A radiation tomography system according to claim 1, wherein the plurality of radiation absorbing members are formed such that an axis cross-section of each of the plurality of radiation absorbing members is substantially circular.

10. A radiation tomography system according to claim 1, wherein the plurality of radiation absorbing members are formed such that an axis cross-section of each of the plurality of radiation absorbing members is substantially rectangular.

11. A radiation detecting device, comprising:
a plurality of radiation detecting elements disposed opposite a radiation source configured to apply radiation to a subject to be imaged;
a plurality of collimator plates partitioning the plurality of radiation detecting elements in a channel direction of the radiation detecting elements, the plurality of collimator plates erected such that plate surfaces of each of the plurality of collimator plates extend along a direction of radiation from the radiation source; and
an aperture-width changing unit configured to change a width of each aperture formed by the plurality of collimator plates by moving a plurality of radiation absorbing members along respective end sides of the collimator plates close to the radiation source, the plurality of radiation absorbing members moveable between a first position at which the end sides are covered and a second position at which the end sides are exposed.

12. A radiation detecting device according to claim 11, wherein the aperture-width changing unit has a plurality of tip portion receiving parts configured to receive respective tip portions of the plurality of radiation absorbing members when the plurality of radiation absorbing members are moved to the first position.

13. A radiation detecting device according to claim 11, wherein the aperture-width changing unit includes a radiation transmittable member configured to guide the plurality of radiation absorbing members along the respective end sides.

14. A radiation detecting device according to claim 12, wherein the aperture-width changing unit includes a radiation transmittable member configured to guide the plurality of radiation absorbing members along the respective end sides.

15. A radiation detecting device according to claim 11, wherein the radiation transmittable member contains carbon fibers.

16. A radiation detecting device according to claim 11, wherein each of the plurality of radiation absorbing members includes a groove into which the end side of the collimator plate fits, and wherein the aperture-width changing unit is configured to move the plurality of radiation absorbing members with the end sides fitted in the grooves, respectively.

17. A radiation detecting device according to claim 11, wherein the plurality of radiation absorbing members contain lead, molybdenum, tungsten, or an alloy of molybdenum or tungsten.

18. A radiation detecting device according to claim 11, wherein the plurality of radiation absorbing members are formed such that each of the axis cross-sections of each of the plurality of radiation absorbing members is substantially circular.

19. A radiation detecting device according to claim 11, wherein the plurality of radiation absorbing members are formed such that each of the axis cross-sections of each of the plurality of radiation absorbing members is substantially rectangular.

20. A method of switching a spatial resolution in radiation tomography using a radiation detecting device, the method comprising:
providing a plurality of radiation detecting elements disposed opposite a radiation source applying radiation to a subject to be imaged;
providing a plurality of collimator plates partitioning the plurality of radiation detecting elements in a channel direction of the radiation detecting elements, the plurality of collimator plates erected such that plate surfaces of each of the plurality of collimator plates extend along a direction of radiation from the radiation source; and
changing a width of each aperture formed by the plurality of collimator plates by moving a plurality of radiation absorbing members along respective end sides of the collimator plates close to the radiation source, the plurality of radiation absorbing members moving between a first position at which the end sides are covered and a second position at which the end sides are exposed.

* * * * *